(12) United States Patent
Rice et al.

(10) Patent No.: US 7,537,528 B2
(45) Date of Patent: *May 26, 2009

(54) METAL WOOD CLUB WITH IMPROVED HITTING FACE

(75) Inventors: Scott A. Rice, San Diego, CA (US); Nicholas M. Nardacci, Bristol, RI (US)

(73) Assignee: Acushnet Company, Fairhaven, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/185,287

(22) Filed: Aug. 4, 2008

(65) Prior Publication Data

US 2008/0293515 A1 Nov. 27, 2008

Related U.S. Application Data

(60) Continuation of application No. 11/780,886, filed on Jul. 20, 2007, now Pat. No. 7,422,527, which is a division of application No. 10/911,422, filed on Aug. 4, 2004, now Pat. No. 7,261,643, which is a continuation-in-part of application No. 10/428,061, filed on May 1, 2003, now Pat. No. 7,029,403, which is a continuation-in-part of application No. 09/551,771, filed on Apr. 18, 2000, now Pat. No. 6,605,007.

(51) Int. Cl.
*A63B 53/04* (2006.01)

(52) U.S. Cl. .................. 473/329; 473/335; 473/345; 473/349

(58) Field of Classification Search ......... 473/324–350, 473/287–292
See application file for complete search history.

(56) References Cited

U.S. PATENT DOCUMENTS 1,318,325 A 10/1919 Klin
1,319,233 A 10/1919 Mattern
1,437,463 A 12/1922 Boye
1,467,435 A 9/1923 Kinnear
1,525,352 A 2/1925 Aitken (Continued)

FOREIGN PATENT DOCUMENTS

| CN | 1114911 | | 1/1996 |
|---|---|---|---|
| GB | 2268693 | A | 1/1994 |
| GB | 2331938 | A | 6/1999 |
| JP | 59207169 | | 11/1984 |
| JP | 61033682 | | 2/1986 |

(Continued)

OTHER PUBLICATIONS

Golf Digest, Sep. 1982, p. 25.
Golf Digest, Dec. 1981, p. 58-59.
"Variable Face Thickness Technology," Calloway Golf advertisement, undated.

*Primary Examiner*—Sebastiano Passaniti
(74) *Attorney, Agent, or Firm*—Kristin D. Wheeler

(57) ABSTRACT

A hitting face of a golf club head having improved flexural stiffness properties. In one embodiment, the hitting face is made from multiple materials. The main portion of the hitting face is a plate-like face made from a first material having a first density. A dense insert made from a second material having a second density that is greater than the first density is attached directly or indirectly to the plate-like face at or near the geometric center thereof. The dense insert increases the flexural stiffness of in a central zone of the hitting face so that a golf club head that has a larger zone of substantially uniform high initial ball speed. In another embodiment, the hitting face includes an insert that includes main plate and at least one wing extending therefrom. The insert is welded to the golf club head so that the main plate does not deflect separately from the remainder of the hitting face. The geometry of the insert controls the stiffness in the axial directions.

10 Claims, 10 Drawing Sheets

U.S. PATENT DOCUMENTS

| | | |
|---|---|---|
| 1,543,691 A | 6/1925 | Beat |
| 1,582,836 A | 4/1926 | Link |
| 1,589,363 A | 6/1926 | Butchart |
| 1,595,589 A | 8/1926 | Tyler |
| 1,605,551 A | 11/1926 | Mattern |
| 1,699,874 A | 1/1929 | Buhrke |
| 1,704,119 A | 3/1929 | Buhrke |
| 1,704,165 A | 3/1929 | Buhrke |
| 1,720,867 A | 7/1929 | Webster et al. |
| 2,034,936 A | 3/1936 | Barnhart |
| 2,087,685 A | 7/1937 | Hackney |
| 3,567,228 A | 3/1971 | Lynn |
| 3,571,900 A | 3/1971 | Hardesty |
| 3,625,518 A | 12/1971 | Solheim |
| 3,659,855 A | 5/1972 | Hardesty |
| 3,863,932 A | 2/1975 | Lezatte |
| 3,985,363 A | 10/1976 | Jepson et al. |
| 4,021,047 A | 5/1977 | Mader |
| 4,023,802 A | 5/1977 | Jepson et al. |
| 4,193,601 A | 3/1980 | Reid, Jr. et al. |
| 4,213,613 A | 7/1980 | Nygren |
| 4,214,754 A | 7/1980 | Zebelean |
| D267,965 S | 2/1983 | Kobayashi |
| 4,429,879 A | 2/1984 | Schmidt |
| 4,449,707 A | 5/1984 | Hayashi et al. |
| 4,451,041 A | 5/1984 | Hayashi et al. |
| 4,451,042 A | 5/1984 | Hayashi et al. |
| 4,465,221 A | 8/1984 | Schmidt |
| 4,471,961 A | 9/1984 | Masghati et al. |
| 4,489,945 A | 12/1984 | Kobayashi |
| 4,511,145 A | 4/1985 | Schmidt |
| 4,762,324 A | 8/1988 | Anderson |
| 4,792,140 A | 12/1988 | Yamaguchi et al. |
| 4,826,172 A | 5/1989 | Antonious |
| 4,842,243 A | 6/1989 | Butler |
| 4,913,438 A | 4/1990 | Anderson |
| 4,915,385 A | 4/1990 | Anderson |
| 4,915,386 A | 4/1990 | Antonious |
| 4,919,430 A | 4/1990 | Antonious |
| 4,919,431 A | 4/1990 | Antonious |
| 4,921,252 A | 5/1990 | Antonious |
| 4,928,965 A | 5/1990 | Yamaguchi et al. |
| 4,930,781 A | 6/1990 | Allen |
| 4,932,658 A | 6/1990 | Antonious |
| 4,955,610 A | 9/1990 | Creighton et al. |
| D312,858 S | 12/1990 | Anderson et al. |
| 5,000,454 A | 3/1991 | Soda |
| 5,024,437 A | 6/1991 | Anderson |
| 5,028,049 A | 7/1991 | McKeighen |
| 5,046,733 A | 9/1991 | Antonious |
| 5,056,705 A | 10/1991 | Wakita et al. |
| 5,060,951 A | 10/1991 | Allen |
| 5,067,715 A | 11/1991 | Schmidt et al. |
| 5,090,702 A | 2/1992 | Viste |
| 5,094,383 A | 3/1992 | Anderson et al. |
| 5,106,094 A | 4/1992 | Desbiolles et al. |
| 5,141,230 A | 8/1992 | Antonious |
| 5,163,682 A | 11/1992 | Schmidt et al. |
| 5,180,166 A | 1/1993 | Schmidt et al. |
| 5,183,255 A | 2/1993 | Antonious |
| 5,213,328 A | 5/1993 | Long et al. |
| 5,221,087 A | 6/1993 | Fenton et al. |
| 5,240,252 A | 8/1993 | Schmidt et al. |
| 5,242,167 A | 9/1993 | Antonious |
| 5,255,918 A | 10/1993 | Anderson et al. |
| 5,261,663 A | 11/1993 | Anderson |
| 5,261,664 A | 11/1993 | Anderson |
| 5,271,621 A | 12/1993 | Lo |
| 5,292,129 A | 3/1994 | Long et al. |
| 5,295,689 A | 3/1994 | Lundberg |
| 5,301,945 A | 4/1994 | Schmidt et al. |
| 5,303,922 A | 4/1994 | Lo |
| 5,318,300 A | 6/1994 | Schmidt et al. |
| 5,328,184 A | 7/1994 | Antonious |
| 5,344,140 A | 9/1994 | Anderson |
| 5,346,218 A | 9/1994 | Wyte |
| 5,351,958 A | 10/1994 | Helmstetter |
| 5,358,249 A | 10/1994 | Mendralla |
| 5,362,047 A | 11/1994 | Shaw et al. |
| 5,362,055 A | 11/1994 | Rennie |
| 5,366,223 A | 11/1994 | Werner et al. |
| 5,380,010 A | 1/1995 | Werner et al. |
| 5,390,924 A | 2/1995 | Antonious |
| 5,395,113 A | 3/1995 | Antonious |
| 5,397,126 A | 3/1995 | Allen |
| 5,401,021 A | 3/1995 | Allen |
| 5,405,136 A | 4/1995 | Hardman |
| 5,405,137 A | 4/1995 | Vincent et al. |
| 5,407,202 A | 4/1995 | Igarashi |
| RE34,925 E | 5/1995 | McKeighen |
| 5,417,419 A | 5/1995 | Anderson et al. |
| 5,417,559 A | 5/1995 | Schmidt |
| 5,423,535 A | 6/1995 | Shaw et al. |
| 5,429,357 A | 7/1995 | Kobayashi |
| 5,431,396 A | 7/1995 | Shieh |
| 5,433,440 A | 7/1995 | Lin |
| 5,447,307 A | 9/1995 | Antonious |
| 5,447,309 A | 9/1995 | Vincent |
| 5,451,056 A | 9/1995 | Manning |
| 5,460,376 A | 10/1995 | Schmidt et al. |
| 5,467,983 A | 11/1995 | Chen |
| 5,470,069 A | 11/1995 | Schmidt et al. |
| 5,474,296 A | 12/1995 | Schmidt et al. |
| 5,482,279 A | 1/1996 | Antonious |
| 5,497,993 A | 3/1996 | Shan |
| 5,505,453 A | 4/1996 | Mack |
| 5,509,660 A | 4/1996 | Elmer |
| 5,522,593 A | 6/1996 | Kobayashi et al. |
| 5,524,331 A | 6/1996 | Pond |
| 5,533,729 A | 7/1996 | Leu |
| 5,536,006 A | 7/1996 | Shieh |
| 5,547,630 A | 8/1996 | Schmidt |
| 5,549,297 A | 8/1996 | Mahaffey |
| 5,564,994 A | 10/1996 | Chang |
| 5,584,770 A | 12/1996 | Jensen |
| 5,595,552 A | 1/1997 | Wright et al. |
| 5,611,741 A | 3/1997 | Schmidt et al. |
| 5,611,742 A | 3/1997 | Kobayashi |
| D379,393 S | 5/1997 | Kubica et al. |
| 5,626,530 A | 5/1997 | Schmidt et al. |
| 5,643,104 A | 7/1997 | Antonious |
| 5,643,108 A | 7/1997 | Cheng |
| 5,643,110 A | 7/1997 | Igarashi |
| 5,649,872 A | 7/1997 | Antonious |
| 5,651,409 A | 7/1997 | Sheehan |
| 5,655,976 A | 8/1997 | Rife |
| 5,669,827 A | 9/1997 | Nagamoto |
| 5,669,829 A | 9/1997 | Lin |
| 5,674,132 A | 10/1997 | Fisher |
| D387,113 S | 12/1997 | Burrows |
| 5,695,411 A | 12/1997 | Wright et al. |
| 5,709,614 A | 1/1998 | Horiba |
| 5,709,615 A | 1/1998 | Liang |
| 5,711,722 A | 1/1998 | Miyajima et al. |
| 5,716,292 A | 2/1998 | Huang |
| 5,718,641 A | 2/1998 | Lin |
| 5,720,673 A | 2/1998 | Anderson |
| 5,743,813 A | 4/1998 | Chen et al. |
| 5,753,170 A | 5/1998 | Muang |
| 5,755,624 A | 5/1998 | Helmstetter |
| 5,762,567 A | 6/1998 | Antonious |
| 5,766,092 A | 6/1998 | Mimeur et al. |
| 5,766,094 A | 6/1998 | Mahaffey et al. |
| 5,766,095 A | 6/1998 | Antonious |

| | | | | | | |
|---|---|---|---|---|---|---|
| 5,776,011 | A | 7/1998 | Su et al. | 7,422,527 B2 * | 9/2008 | Rice et al. ............ 473/329 |
| 5,807,190 | A | 9/1998 | Krumme et al. | 2004/0266548 A1 | 12/2004 | Cheng et al. |
| 5,827,132 | A | 10/1998 | Bamber | | | |
| RE35,955 | E | 11/1998 | Lu | FOREIGN PATENT DOCUMENTS | | |
| D401,652 | S | 11/1998 | Burrows | | | |
| 5,830,084 | A | 11/1998 | Kosmatka | JP | 61162967 | 7/1986 |
| 5,839,975 | A | 11/1998 | Lundberg | JP | 61181477 | 8/1986 |
| 5,842,934 | A | 12/1998 | Ezaki et al. | JP | 61185281 | 8/1986 |
| 5,851,159 | A | 12/1998 | Burrows | JP | 61240977 | 10/1986 |
| 5,863,261 | A | 1/1999 | Eggiman | JP | 1244770 | 9/1989 |
| 5,873,791 | A | 2/1999 | Allen | JP | 02130519 | 5/1990 |
| 5,873,795 | A | 2/1999 | Wozny et al. | JP | 4020357 | 1/1992 |
| D406,294 | S | 3/1999 | Burrows | JP | 4327864 | 11/1992 |
| 5,888,148 | A | 3/1999 | Allen | JP | 5212526 | 8/1993 |
| 5,890,973 | A | 4/1999 | Gamble | JP | 05237207 | 9/1993 |
| D411,272 | S | 6/1999 | Burrows | JP | 6007487 | 1/1994 |
| 5,908,357 | A | 6/1999 | Hsieh | JP | 06031016 | 2/1994 |
| 5,921,872 | A | 7/1999 | Kobayashi | JP | 6114126 | 4/1994 |
| 5,931,746 | A | 8/1999 | Soong | JP | 6126002 | 5/1994 |
| 5,935,019 | A | 8/1999 | Yamamoto | JP | 6154367 | 6/1994 |
| 5,938,541 | A | 8/1999 | Allen et al. | JP | 6182005 | 7/1994 |
| 5,941,782 | A | 8/1999 | Cook | JP | 6269518 | 9/1994 |
| 5,944,619 | A | 8/1999 | Cameron | JP | 8168541 | 7/1996 |
| 5,954,596 | A | 9/1999 | Noble et al. | JP | 8243194 | 9/1996 |
| D415,807 | S | 10/1999 | Werner et al. | JP | 8280853 | 10/1996 |
| 5,961,394 | A | 10/1999 | Minabe | JP | 8280854 | 10/1996 |
| 5,967,905 | A | 10/1999 | Nakahara et al. | JP | 8294550 | 11/1996 |
| 5,971,868 | A | 10/1999 | Kosmatka | JP | 9028842 | 2/1997 |
| 5,993,329 | A | 11/1999 | Shich | JP | 9047531 | 2/1997 |
| 6,007,432 | A | 12/1999 | Kosmatka | JP | 9154985 | 6/1997 |
| 6,027,416 | A | 2/2000 | Schmidt et al. | JP | 9168613 | 6/1997 |
| 6,139,445 | A | 10/2000 | Werner et al. | JP | 9192270 | 7/1997 |
| 6,152,833 | A | 11/2000 | Werner et al. | JP | 9192273 | 7/1997 |
| 6,248,025 | B1 | 6/2001 | Murphy | JP | 9239074 | 9/1997 |
| 6,319,150 | B1 | 11/2001 | Werner et al. | JP | 9239075 | 9/1997 |
| 6,338,683 | B1 | 1/2002 | Kosmatka | JP | 9248353 | 9/1997 |
| 6,368,234 | B1 | 4/2002 | Galloway | JP | 2717759 | 11/1997 |
| 6,381,828 | B1 | 5/2002 | Boyce | JP | 9294833 | 11/1997 |
| 6,390,933 | B1 | 5/2002 | Galloway | JP | 9299519 | 11/1997 |
| 6,398,666 | B1 | 6/2002 | Evans et al. | JP | 10024126 | 1/1998 |
| 6,435,982 | B1 | 8/2002 | Galloway et al. | JP | 10024128 | 1/1998 |
| 6,506,129 | B2 | 1/2003 | Chen | JP | 10085369 | 4/1998 |
| 6,605,007 | B1 | 8/2003 | Bissonnette et al. | JP | 10118227 | 5/1998 |
| 6,626,769 | B1 | 9/2003 | Lin | JP | 10137372 | 5/1998 |
| 6,648,774 | B1 | 11/2003 | Lee | JP | 10155943 | 6/1998 |
| 6,663,501 | B2 | 12/2003 | Chen | JP | 10258142 | 9/1998 |
| 6,669,576 | B1 | 12/2003 | Rice | JP | 10263121 | 10/1998 |
| 6,755,627 | B2 | 6/2004 | Chang | JP | 10323410 | 12/1998 |
| 6,994,636 | B2 | 2/2006 | Hocknell et al. | JP | 10337347 | 12/1998 |
| 7,029,403 | B2 | 4/2006 | Rice et al. | | | |
| 7,261,643 | B2 * | 8/2007 | Rice et al. ............ 473/329 | * cited by examiner | | |

METAL WOOD CLUB WITH IMPROVED HITTING FACE

CROSS-REFERENCE TO RELATED APPLICATION

The present application is a continuation of U.S. application Ser. No. 11/780,886 filed on Jul. 20, 2007 now U.S. Pat. No. 7,422,527, which is a divisional of U.S. application Ser. No. 10/911,422 filed on Aug. 4, 2004 and issued as U.S. Pat. No. 7,261,643 on Aug. 28, 2007, which is continuation-in-part of U.S. application Ser. No. 10/428,061 filed on May 1, 2003 and issued as U.S. Pat. No. 7,029,403 on Apr. 18, 2006, which is a continuation-in-part of U.S. application Ser. No. 09/551,771 filed on Apr. 18, 2000 and issued as U.S. Pat. No. 6,605,007 on Aug. 12, 2003, the disclosures of which are incorporated herein by reference in their entireties.

FIELD OF THE INVENTION

The present invention relates to an improved golf club head. More particularly, the present invention relates to a golf club head with an improved striking face having a relatively large zone of high initial ball velocity.

BACKGROUND

The complexities of golf club design are well known. The specifications for each component of the club (i.e., the club head, shaft, grip, and subcomponents thereof) directly impact the performance of the club. Thus, by varying the design specifications, a golf club can be tailored to have specific performance characteristics.

The design of club heads has long been studied. Among the more prominent considerations in club head design are loft, lie, face angle, horizontal face bulge, vertical face roll, center of gravity, inertia, material selection, and overall head weight. While this basic set of criteria is generally the focus of golf club engineering, several other design aspects must also be addressed. The interior design of the club head may be tailored to achieve particular characteristics, such as the inclusion of hosel or shaft attachment means, perimeter weights on the club head, and fillers within hollow club heads.

Golf club heads must also be strong to withstand the repeated impacts that occur during collisions between the golf club and the golf ball. The loading that occurs during this transient event can create a peak force of over 2,000 lbs. Thus, a major challenge is designing the club face and body to resist permanent deformation or failure by material yield or fracture. Conventional hollow metal wood drivers made from titanium typically have a uniform face thickness exceeding 2.5 mm to ensure structural integrity of the club head.

Players generally seek a metal wood driver and golf ball combination that delivers maximum distance and landing accuracy. The distance a ball travels after impact is dictated by the magnitude and direction of the ball's translational velocity and the ball's rotational velocity or spin. Environmental conditions, including atmospheric pressure, humidity, temperature, and wind speed, further influence the ball's flight. However, these environmental effects are beyond the control of the golf equipment manufacturer. Golf ball landing accuracy is driven by a number of factors as well. Some of these factors are attributed to club head design, such as center of gravity and club face flexibility.

The United States Golf Association (USGA), the governing body for the rules of golf in the United States, has specifications for the performance of golf balls. These performance specifications dictate the size and weight of a conforming golf ball. One USGA rule limits the golf ball's initial velocity after a prescribed impact to 250 feet per second ±2% (or 255 feet per second maximum initial velocity). To achieve greater golf ball travel distance, ball velocity after impact and the coefficient of restitution of the ball-club impact must be maximized while remaining within this rule.

Generally, golf ball travel distance is a function of the total kinetic energy imparted to the ball during impact with the club head, neglecting environmental effects. During impact, kinetic energy is transferred from the club and stored as elastic strain energy in the club head and as viscoelastic strain energy in the ball. After impact, the stored energy in the ball and in the club is transformed back into kinetic energy in the form of translational and rotational velocity of the ball, as well as the club. Since the collision is not perfectly elastic, a portion of energy is dissipated in club head vibration and in viscoelastic relaxation of the ball. Viscoelastic relaxation is a material property of the polymeric materials used in all manufactured golf balls.

Viscoelastic relaxation of the ball is a parasitic energy source, which is dependent upon the rate of deformation. To minimize this effect, the rate of deformation must be reduced. This may be accomplished by allowing more club face deformation during impact. Since metallic deformation may be purely elastic, the strain energy stored in the club face is returned to the ball after impact thereby increasing the ball's outbound velocity after impact.

A variety of techniques may be utilized to vary the deformation of the club face, including uniform face thinning, thinned faces with ribbed stiffeners and varying thickness, among others. These designs should have sufficient structural integrity to withstand repeated impacts without permanently deforming the club face. In general, conventional club heads also exhibit wide variations in initial ball speed after impact, depending on the impact location on the face of the club. Hence, there remains a need in the art for a club head that has a larger "sweet zone" or zone of substantially uniform high initial ball speed.

SUMMARY OF THE INVENTION

The present invention relates to a golf club head adapted for attachment to a shaft. An embodiment of the present invention is a golf club head that includes a hitting face made from multiple materials, wherein the first material forms a central zone of the hitting face. The central zone has a first flexural stiffness. The second material forms an intermediate zone of the hitting face concentric with the central zone. The intermediate zone has a second flexural stiffness that is lower than the first flexural stiffness.

Another embodiment of the present invention is a golf club head that includes a crown forming an upper surface of the golf club head, a sole forming a lower surface of the golf club head, and a hitting face disposed between the crown and the sole, wherein the hitting face includes a face insert welded around the perimeter thereof to the golf club head. The face insert includes a main plate and at least one wing extending therefrom.

BRIEF DESCRIPTION OF THE DRAWINGS

Preferred features of the present invention are disclosed in the accompanying drawings, wherein similar reference characters denote similar elements throughout the several views, and wherein:

FIG. 12b is a bottom perspective view of the club head shown in FIG. 12a;

FIG. 13b is a bottom perspective view of the club head shown in FIG. 13a;

DETAILED DESCRIPTION OF THE PREFERRED EMBODIMENT

Priority U.S. Pat. No. 6,605,007, which has been incorporated herein in its entirety, discloses an improved golf club that also produces a relatively large "sweet zone" or zone of substantially uniform high initial velocity or high coefficient of restitution (COR).

COR or coefficient of restitution is a measure of collision efficiency. COR is the ratio of the velocity of separation to the velocity of approach. In this model, therefore, COR was determined using the following formula:

$$(v_{club\text{-}post} - v_{ball\text{-}post})/(v_{ball\text{-}pre} - v_{club\text{-}pre})$$

where, $v_{club\text{-}post}$ represents the velocity of the club after impact;
$v_{ball\text{-}post}$ represents the velocity of the ball after impact;
$v_{club\text{-}pre}$ represents the velocity of the club before impact (a value of zero for USGA COR conditions); and
$v_{ball\text{-}pre}$ represents the velocity of the ball before impact.

COR, in general, depends on the shape and material properties of the colliding bodies. A perfectly elastic impact has a COR of one (1.0), indicating that no energy is lost, while a perfectly inelastic or perfectly plastic impact has a COR of zero (0.0), indicating that the colliding bodies did not separate after impact resulting in a maximum loss of energy. Consequently, high COR values are indicative of greater ball velocity and distance.

Figure 1:
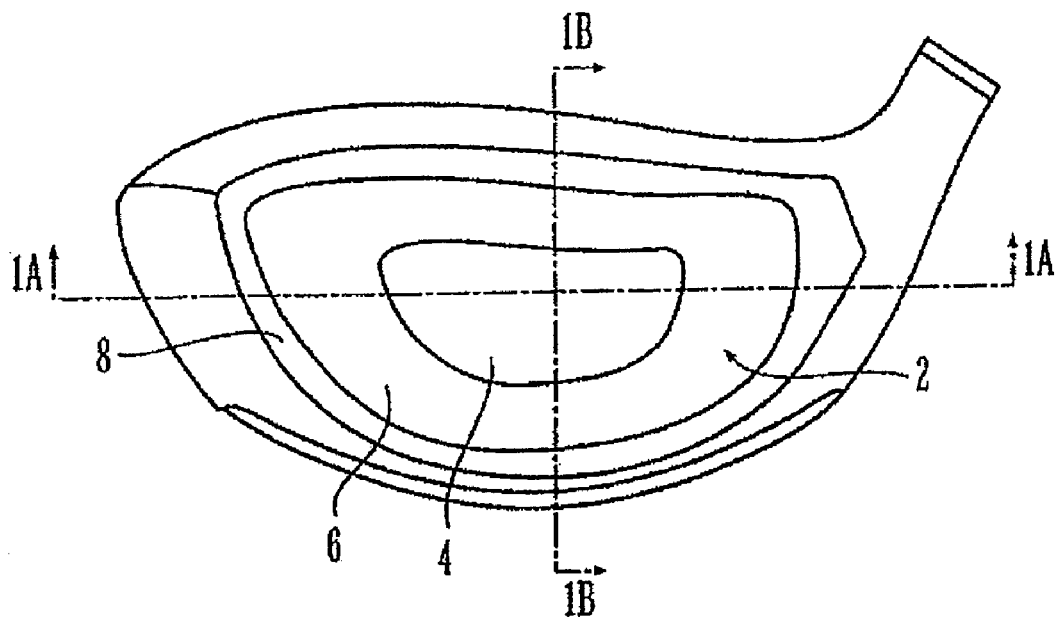
FIG. 1 is a front view of a striking face of the golf club head disclosed in the parent patent application.
Figure 1A:
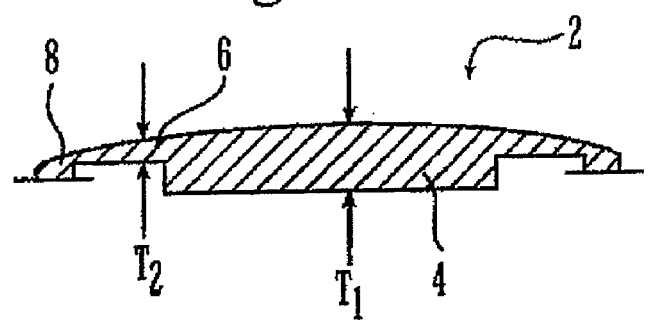
FIGS. 1a and 1b are cross-sectional views of the striking face of FIG. 1 taken along lines 1A-1A and 1B-1B, respectively.
Figure 1B:
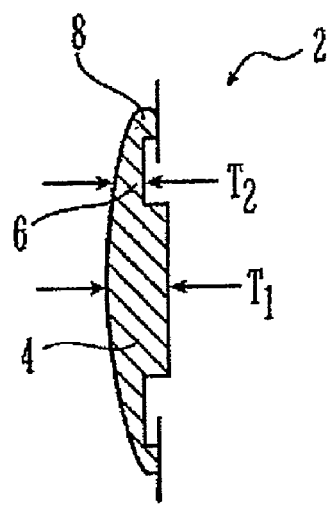

As shown in FIGS. 1, 1a and 1b, the accuracy of the club and the club's large zone of uniform high initial velocity are produced by hitting face 2, having central zone 4, a surrounding intermediate zone 6, and an optional perimeter zone 8. Preferably, the area of central zone 4 comprises about 15% to about 60% of the total area of the hitting face 2, and more preferably about 20% to about 50%.

Central zone 4 is comparatively rigid and intermediate zone 6 is relatively flexible so that upon ball impact, intermediate zone 6 of face 2 deforms to provide high ball velocity, while central zone 4 is substantially undeformed so that the ball flies on-target. Thus, upon ball impact the deformation of intermediate zone 6 allows central zone 4 to move into and out of a club head 10 as a unit. Surrounding intermediate zone 6 may be located adjacent to central zone 4, and optional perimeter zone 8 may be located adjacent to intermediate zone 6. As a result, the head exhibits a coefficient of restitution greater than about 0.81.

The above is accomplished by providing central zone 4 with a first flexural stiffness and intermediate zone 6 with a second flexural stiffness. Flexural stiffness (FS) is defined as each portion's average elastic modulus (E) times each portion's average thickness (t) cubed or ($FS=Et^3$). The calculation of averages of modulus and thickness is fully disclosed in the parent application and in the '007 patent, which have already been incorporated by reference in their entireties. The determination of FS when the thickness varies or when the material is anisotropic is also fully discussed in the parent patent application and in the '007 patent.

Since the flexural stiffness is a function of material and thickness, the following techniques can be used to achieve the substantial difference between the flexural stiffness of central zone 4 and intermediate zone 6: 1) different materials can be used for each portion, 2) different thicknesses can be used for each portion, or 3) different materials and thickness can be used for each portion. For example, in a preferred embodiment, the thickness of the central zone is greater than the thickness of the intermediate zone and the material for both portions is the same.

In club head 10, the above flexural stiffness relationships can be achieved by selecting a certain material with a particular elastic modulus and varying the thickness of the zones. In another embodiment, the flexural stiffness relationships can be achieved by varying the materials of the zones with respect to one another so that the zones have different elastic moduli and the thickness is changed accordingly. Thus, the thickness of the zones can be the same or different depending on the elastic modulus of the material of each zone. It is also possible to obtain the required flexural stiffness ratio through the use of structural ribs, reinforcing plates, and thickness parameters. The parent case application and the grandparent '007 patent describe in detail the preferred ranges of ratios of flexural stiffness between central zone 4 and intermediate zone 6.

Figure 1C:
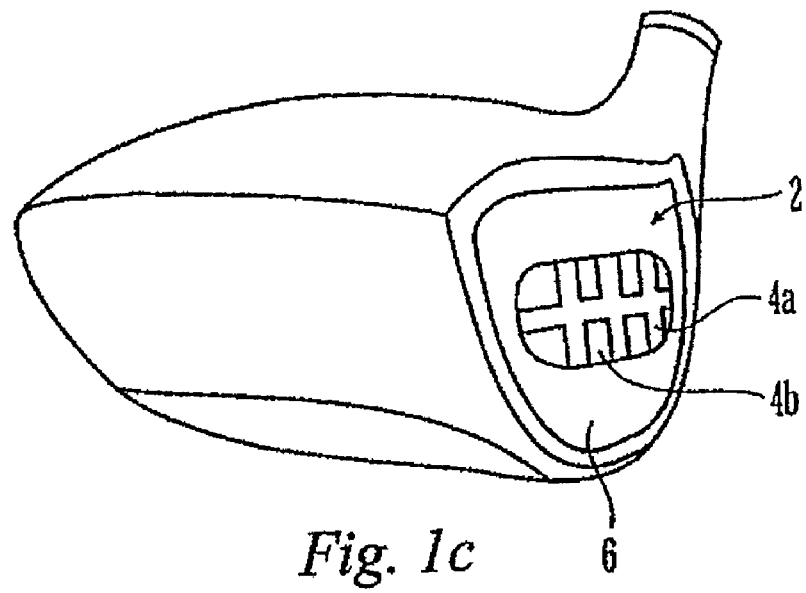
FIG. 1c is an alternate embodiment from the priority patent.

Further, as discussed in the '007 patent, two or more different homogeneous materials may be used to form hitting face 2. For example, central zone 4 may be of generally uniform thickness and made from a stainless steel having a Young's Modulus of $30.0 \times 10^6$ lbs/in². The adjacent intermediate zone 6 has a continuously tapering thickness from the pace perimeter toward central zone 4. The thickness of intermediate zone 6 is defined to change linearly. Intermediate zone 6 is made from a titanium alloy having a Young's Modulus of $16.5 \times 10^6$ lbs/in$^2$. Alternatively, as shown in FIG. 1c, which corresponds to FIG. 10 from the '007 patent, central zone 4 may include ribs 4a made of stainless steel having a Young's Modulus of $3.0 \times 10^6$ lbs/in$^2$ with a titanium alloy having a Young's Modulus of $16.5 \times 10^6$ lbs/in$^2$ in the interstitial spaces 4b. Intermediate zone 6 is made from the same titanium alloy. The flexural stiffness ratio between central zone 4 and intermediate zone 6 is calculated in detail in the '007 patent.

Optional perimeter zone 8 preferably increases in thickness compared to intermediate zone 6 to increase the flexural stiffness thereof. Alternatively, optional perimeter zone 8 may increase in flexural stiffness compared to intermediate zone by forming perimeter zone 8 out of a different material than that of intermediate zone 6. For example, perimeter zone 8 may be made of the same material as central zone 4. Alternatively, perimeter zone 8 may be made of an entirely different material than that of central zone 4 or intermediate zone 6. Perimeter zone 8 would then be attached to intermediate zone 6, such as by welding.

Figure 2:
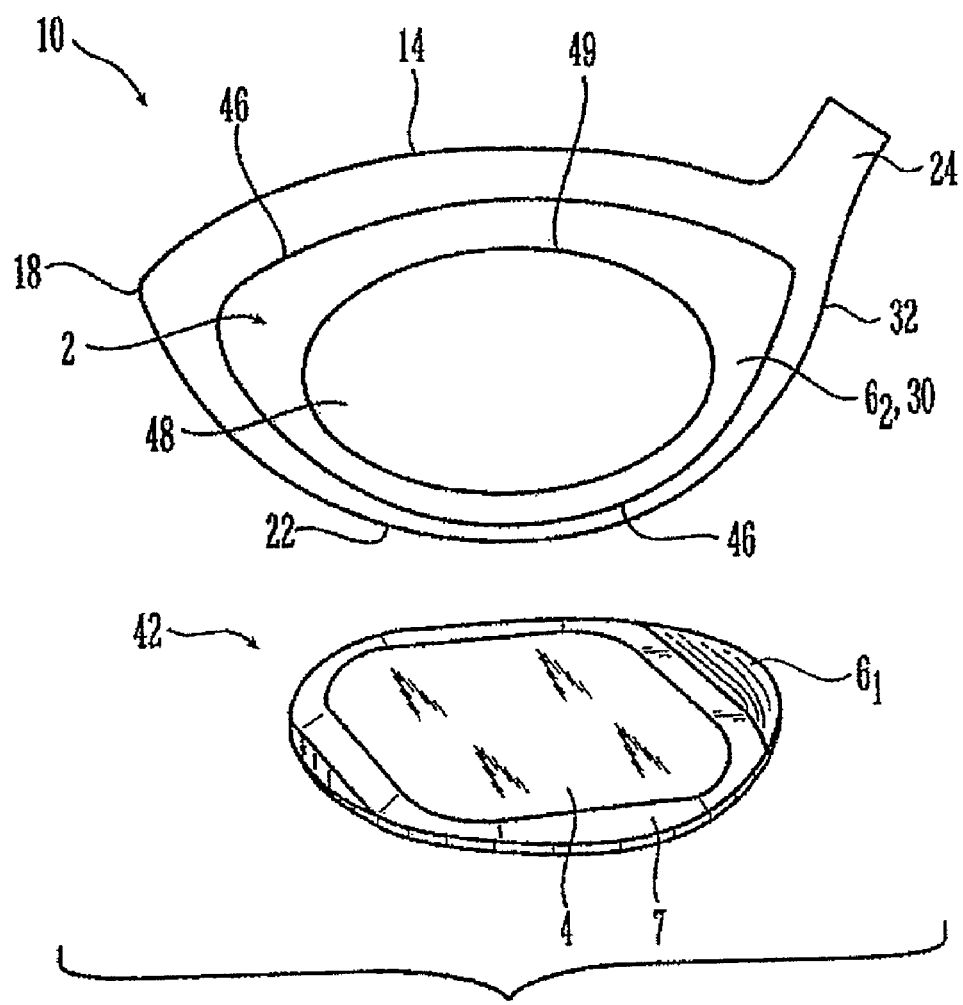
FIG. 2 is a front, exploded view of an alternate embodiment of the parent patent invention.
Figure 8:
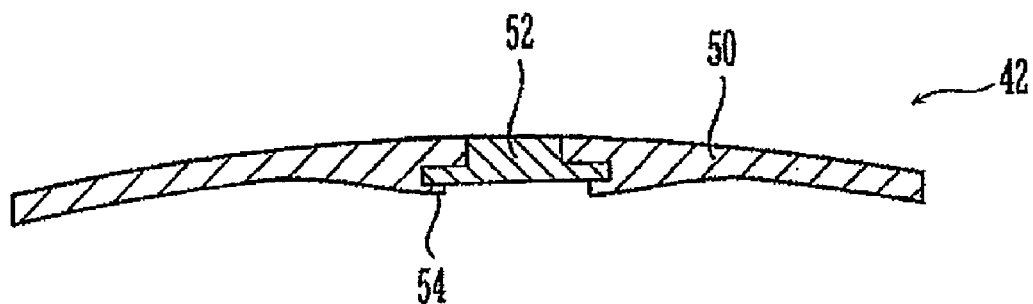
FIG. 8 is a cross-sectional view of another alternate embodiment of a hitting face of the present invention.

Referring now to FIG. 2, which corresponds to FIG. 8 from the parent case, hitting face 2 may comprise a face insert 42, which is welded onto a cavity defined on the face. Hitting face 2 may comprise a face insert 42 and face support 30. In this embodiment, hitting face 2 is delineated from crown 14, toe 18, sole 22 and heel 32 by parting line 46. Central zone 4 is preferably disposed on the inner-cavity-facing surface of face insert 42, and, as shown, has a generally elliptical shape. The elliptical central zone 4 is fully disclosed in the parent patent application. Central zone 4 is preferably aligned in the direction of the low toe to high heel, so that a high COR zone can be established in the direction of high tow to low heel. This high COR zone advantageously coincides with the typical impact patterns created by golfers.

As defined in the parent case, the term "ellipse" or "elliptical" refers to non-circular shapes that have discernable major axis and minor axis, and include, but are not limited to, any quadrilateral shapes, geometrical ellipses, quadrilateral shapes with one or more rounded corner(s) and unsymmetrical elliptical shapes. The "major axis" is defined as the axis coinciding with the longest length that can be drawn through the non-circular shapes without intersecting the perimeter of the shapes at more than two locations, i.e., at the start and end points of said length. The "minor axis" is orthogonal to the major axis at or near its midpoint. As used herein, the term "concentric" refers to shapes that substantially encircle or surround other shapes.

Intermediate zone 6, designated as 6$_1$ and 6$_2$, can be disposed partially on face insert 42 and partially on face support 30. A transition zone 7 having variable thickness is disposed between central zone 4 and intermediate zone 6. Preferably, the thickness of central zone 4 is reduced to the lesser thickness of intermediate zone 6 within transition zone 7. This reduces any local stress-strain caused by impacts with golf balls due to abrupt changes in thickness. Face support 30 defines hole 48, which is bordered by rim 49. Face insert 42 can be attached to face support 30 by welding at or around rim 49.

Preferably, face insert 42 is made by milling or stamping and forming. In the manufacturing process, a malleable metal suitable for use as a hitting face, such as titanium, titanium alloy, carbon steel, stainless steel, beryllium copper, and other forgeable metals, is heated and then hammered into the desired shape of the face cup. Examples of some appropriate metals include but are not limited to titanium 6-4 alloy, titanium 15-3-3-3 alloy, titanium 20-4-1 alloy, and DAT 55 and DAT 55G, titanium alloys available from Diado Steel of Tokyo, Japan.

The preferred forging process is die or billet forging, in which a pre-measured rod of forgeable metal is heated and placed between a die, which contains the desired shape of face insert 42, and a hammer. The heated metal is then hammered into the desired shape. An advantage of forging face insert 42 is that the thickness of the face can be as thin as about 0.060 inch (or about 1.5 mm) around the perimeter or edge thereof.

Figure 3:
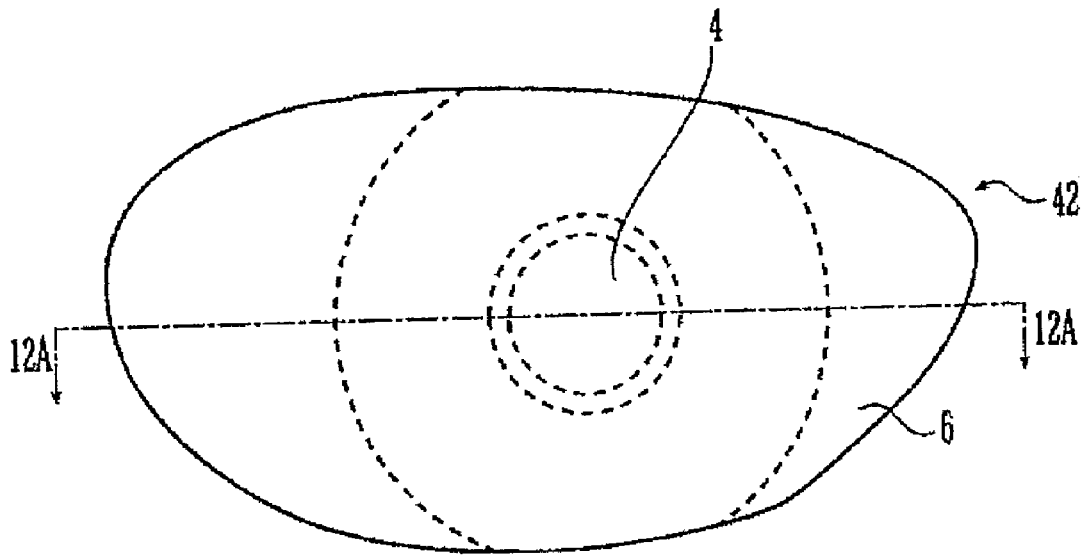
FIG. 3 is a front plan view of an embodiment of a hitting face of the present invention.
Figure 3A:
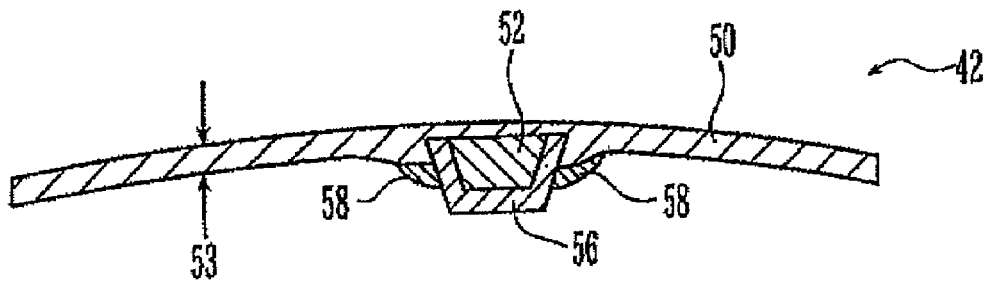
FIG. 3A is a cross-sectional view of the hitting face of FIG. 3 taken along line 3A-3A.

Referring now to FIGS. 3-8, alternate embodiments of hitting face insert 42 are shown. In these embodiments, the flexural stiffness of central zone 4 is higher than the flexural stiffness of intermediate area 6 due to a dense insert 52 made of a material of greater density than that of the material forming the remainder of face insert 42. A cross-sectional view of a preferred embodiment of the present invention is shown in FIG. 3A, wherein face insert 42 includes a plate-like face 50 and an insert 52.

Plate-like face 50 is preferably elliptical in shape with a slightly curved profile, although any shape may be used, such as polygonal, circular or irregular.

The size of plate-like face 50 depends upon the overall size of golf club head 10. However, in a preferred embodiment, plate-like face 50 measures between 80 and 100 mm along the long axis of the ellipse and between 35 and 60 mm along the short axis of the ellipse. More preferably, plate-like face 50 measures 90 mm along the long axis of the ellipse and 50 mm along the short axis. Plate-like face 50 may be of uniform or non-uniform thickness 53. In one embodiment, thickness 53 ranges from 2-5 mm. Preferably, thickness 53 is 2.7 mm gradually tapering to a maximum thickness of 4.5 mm.

Figure 3B:
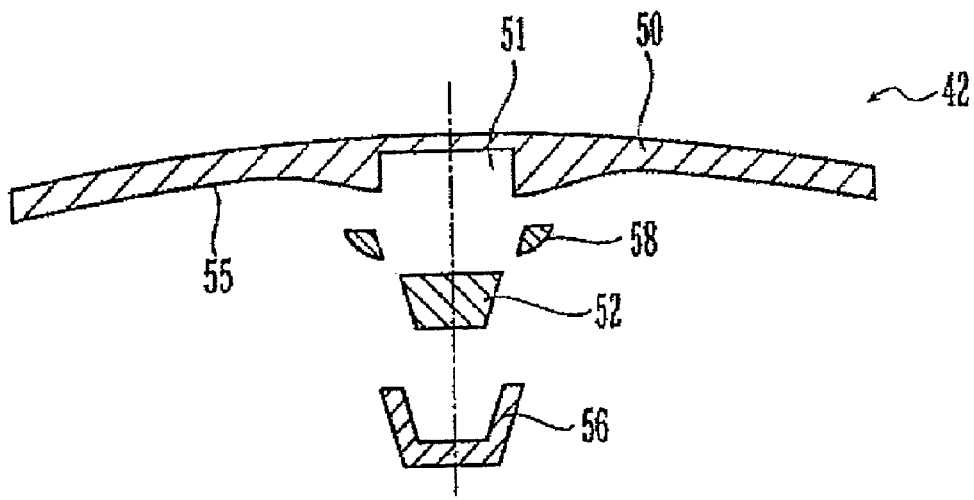
FIG. 3B is an exploded cross-sectional view of the hitting face of FIG. 3.

Plate-like face 50 preferably includes a cavity 51, shown in the exploded view of FIG. 3B, formed on the surface 55 that faces the inner cavity of golf club head 10. Further, in the vicinity of cavity 51, plate-like face 50 preferably increases in thickness, so as to combine the effects of a thickened central zone as described above with the effects of the denser material of dense insert 52. In this embodiment, cavity 51 is circular in shape, although the shape of cavity 51 is preferably chosen to correspond to the cross-sectional shape of dense insert 52. Although cavity 51 may be made of any size sufficient to accommodate dense insert 52, in one embodiment, cavity 51 has an interior width of approximately 14 mm and a depth of approximately 2 mm.

As discussed above, plate-like face 50 is preferably forged, although stamping and casting are also suitable manufacturing techniques. Plate-like face 50 may be made of any material discussed herein that is suitable for forming hitting face 2, such as titanium, titanium alloy, carbon steel, stainless steel, beryllium copper. The more preferred metal is titanium 6-4 alloy, as described above.

Dense insert 52 is shown as being a conical frusta that is relatively small in cross-sectional surface area compared to plate-like face 50. Dense insert 52 may take on any shape that is convenient for manufacturing, for example a cylinder or a circular, elliptical or quadrilateral disk. Dense insert 52 is made of a material of greater density than that of plate-like face 50, preferably tungsten or stainless steel, although any material of greater density than plate-like face 50 is appropriate for use in the present invention, including copper, nickel, and bronze. Dense insert 52 may be milled, stamped from sheet metal, forged, die cut, cast, or made using any technique known in the art.

Dense insert 52 is preferably small compared to the size of plate-like face 50. In the preferred embodiment, dense insert 52 is approximately 10 mm in diameter at its widest point and approximately 7 mm in height. As such, dense insert 52 protrudes from surface 55 of plate-like face 50, as dense insert 52 is of a greater height than the depth of cavity 51. The size of dense insert 52 may be varied so as to control the effective size of central zone 4.

Dense insert 52 may be directly or indirectly affixed to plate-like face 50. In the preferred embodiment, dense insert 52 is contained within a cap 56 made of the same material as that used to make plate-like face 50 so that cap 56 may be readily welded to plate-like face 50. Dense insert 52 may be affixed to an interior surface of cap 56, adhered to at least one interior surface of cap 56, or simply rest within cap 56. As shown, cap 56 is a conical frusta having an interior cavity shaped so that dense insert 52 fits tightly within cap 56. Cap 56 may be made using any method known in the art, such as casting, stamping or forging.

As such, dense insert 52 is indirectly fixedly attached to plate-like face 50, in that dense insert 52 is contained within cap 56 which is joined to plate-like face 50 by a weld bead 58 so that dense insert 52 is not dislodged from its position during the repeated impacts of hitting face 2 with golf balls. Alternately, at least a portion of the combination of dense insert 52 and cap 56 may be secured within cavity 51 using an adhesive, for example hot melt adhesives, epoxy adhesives, polyurethane adhesives, sealants, thermoset adhesives, UV curing adhesives, silicon adhesives, acrylic and cyanoacrylic adhesives.

Figure 4:
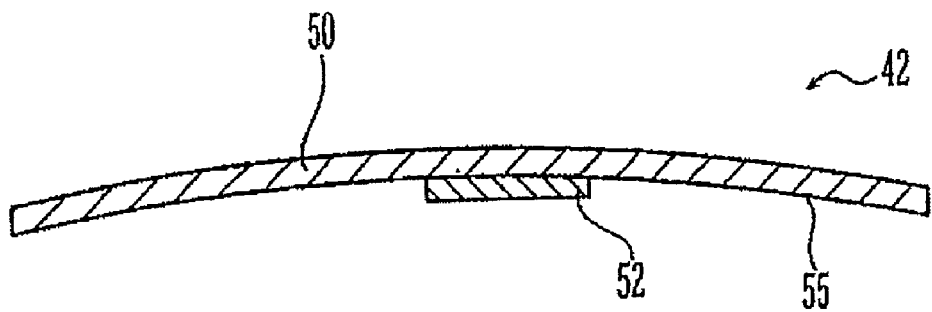
FIG. 4 is a cross-sectional view of an alternate embodiment of a hitting face of the present invention.

Referring to FIG. 4, an alternate embodiment of face insert 42 having a dense insert 52 is shown. In this embodiment, dense insert 52 is a circular disk that is adhered directly to the inner cavity-facing surface 55 of plate-like face 50. Alternatively, dense insert 52 may also be welded to the surface of plate-like face 50.

Figure 5:
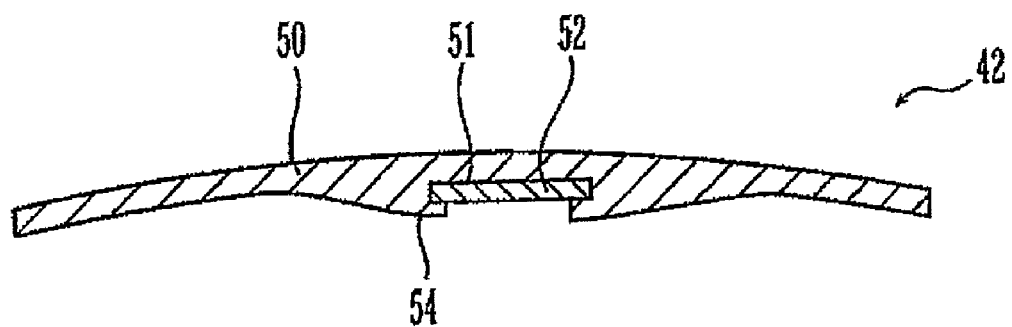
FIG. 5 is a cross-sectional view of another alternate embodiment of a hitting face of the present invention.

Referring to FIG. 5, another alternate embodiment of face insert 42 having a dense insert 52 is shown. In this embodiment, plate-like face 50 includes a cavity 51 into which dense insert 52 in the shape of a circular disk in inserted. Dense insert 52 may or may not be affixed to the surface of cavity 51, such as with an adhesive. A flange portion 54 extends over dense insert 52 to hold dense insert 52 within cavity 51, i.e., to prevent dense insert 52 from being ejected from cavity 51 during repeated impacts with golf balls. Flange portion 54 may be a piece of material welded to plate-like face 50. Alternatively, flange portion 54 may be formed during manufacturing of plate-like face 50. Face insert 42 is preferably milled and/or stamped. During the manufacturing process, cavity 51 is formed in a thickened central zone of plate-like face 50. Cavity 51 is formed to a height that is slightly higher than the height of dense insert 52. Dense insert 52 is then positioned within cavity 51 and preferably adhered to an inner surface of cavity 51. The surface of plate-like face 50 is then forcibly struck or hammered to deform the portion cavity 51 protruding over dense insert 52, thereby forming flange portion 54.

Figure 6:
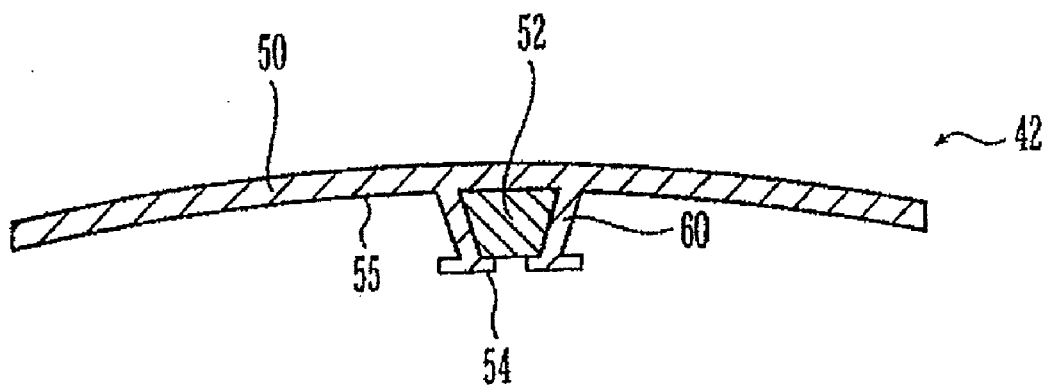
FIG. 6 is a cross-sectional view of another alternate embodiment of a hitting face of the present invention.

Referring to FIG. 6, another alternate embodiment of multiple-material face insert 42 is shown. This embodiment includes a plate-like face 50 similar to the plate-like faces of earlier-described embodiments. However, in this embodiment, plate-like face includes a thin-walled cup-like protrusion 60 extending outward from the inner cavity-facing surface 55 of plate-like face 50. Cup-like protrusion 60 is shown as a frusta, although it may have any shape, such as a hollow cylinder, three-dimensional polygon, or an irregular shape.

Dense insert 52, similar to the dense inserts described above, is sized and dimensioned to fit tightly within cup-like protrusion 60. Dense insert 52 may be affixed to the interior of cup-like protrusion 60 using, for example, an adhesive. However, dense insert 52 is held within cup-like protrusion 60 by flange portion 54, similar to earlier-discussed flange portions. In this embodiment, however, if the stamping technique is used to form flange portion 54, the excess material comes from the excess height of cup-like protrusion 60.

Figure 7:
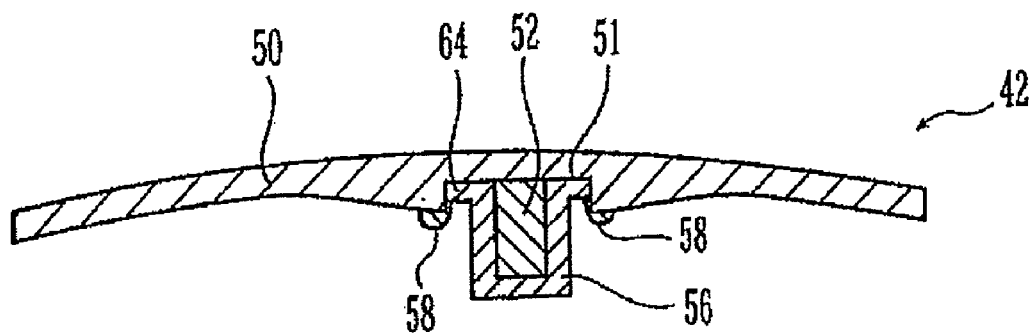
FIG. 7 is a cross-sectional view of another alternate embodiment of a hitting face of the present invention.

Referring to FIG. 7, a cross-sectional view of another alternate embodiment of a face insert 42 of the present invention is shown. In this embodiment, plate-like face 50 is similar to the plate-like face described above with respect to the preferred embodiment. In this embodiment, however, cap 56 is a hollow cylinder having an outer diameter that is less than the diameter of cavity 51. Dense insert 52 is a cylindrical plug that fits tightly within cap 56, preferably affixed therewithin.

Cap 56 includes a brim 64 that is sized and dimensioned to fit snugly within cavity 51. As such, a small amount of clearance exists between the outer diameter of cap 56 and the edge of cavity 51. Weld bead 58 is formed around the edge of cavity 51 and the edge of brim 64 to attach cap 56 to plate-like face 50. This geometry of cap 56 increases the surface area to which weld bead 58 may affix, thereby increasing the strength of the joint. As such, the usable life of hitting face 2 increases, as the stronger joint is less likely to suffer failure and eject dense insert 52 into the inner cavity of golf club head 10.

Figure 8A:
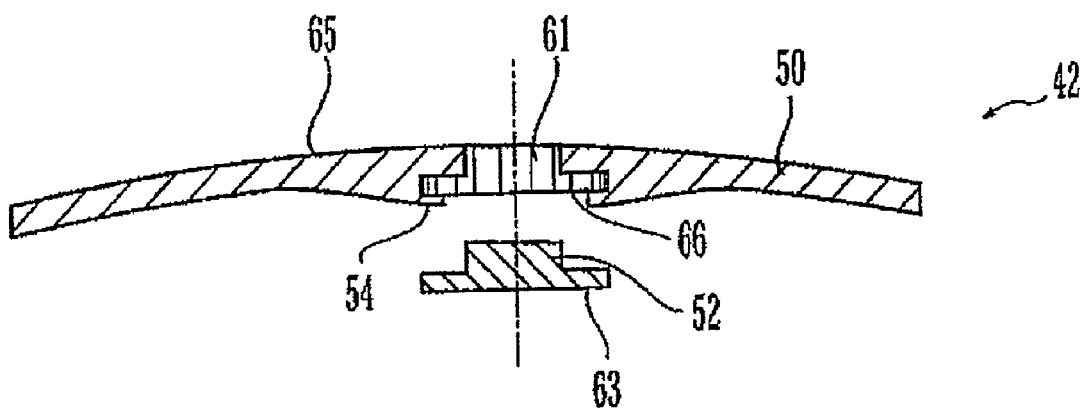
FIG. 8A is an exploded cross-sectional view of the hitting face of FIG. 8.

Referring now to FIGS. 8 and 8A, yet another alternate embodiment of a face insert 42 of the present invention is shown. In this embodiment, face insert 42 includes plate-like face 50 and a dense insert 52. However, a void 61 is formed at or near the center of plate-like face 50 extending entirely through the thickness thereof. Dense insert 52 is preferably configured such that at least a portion thereof is fitted into void 61 while a brim portion 63 thereof rests upon or is affixed to a lip or shelf 66 formed in void 61. A flange portion 54, similar to those flange portions described above, holds dense insert 52 securely in place. As such, dense insert 52 is visible from the exterior-facing surface 65 of plate-like face 50. Although the exterior-facing surface of dense insert 52 is shown as being substantially flush with surface 65, this need not be the case and a gap may exist between the edges of void 61 such that dense insert 52 is still visible.

EXAMPLE

Inventive Club W is a hollow metal wood club head made generally in accordance with the embodiment shown in FIG. 7. Club W includes a face insert made of a plate of titanium alloy having a tungsten insert welded to the inner-cavity-facing surface thereof at or near the geometric center of the plate. As such, the thickness of Club W varies in that the central zone of the face insert is thicker than the perimeter thereof. Club W has a COR measured to be 0.812.

A standard King Cobra® SZ 440 club head is also a hollow metal wood club head. The SZ 440 club head has a hitting face having variable thickness. Similar to Club W, the SZ 440 club head is thicker near the geometric center of the hitting face and thinner toward the perimeter thereof. However, the thickness variations of the SZ 440 club head hitting face are manufactured integrally with the hitting face, i.e., the hitting face includes a single plate of material that is machined to remove a portion of the material only around the perimeter of the plate. The SZ 440 club head has a COR of 0.814, approximately equal to that of Club W.

Both clubs were tested using the pendulum test, which is the standard test for club face flexibility or trampoline effect under USGA and international rules. This test entails impacting a specific spot golf club head several times using a small steel pendulum. A characteristic time between the club head and the pendulum is recorded in microseconds (μs), thereby determining the flexibility of the golf club head at that point. In accordance with USGA rules, nine points on the golf club head are so tested. Generally, the longer the characteristic time, the greater the flexibility of the golf club head.

As shown in Table 1, the characteristic time of the pendulum with Club W is greater than that of the SZ 440 club face at all tested points. As such, the flexibility of Club W is greater than that of the SZ 440 club face, even though the COR value is approximately the same for both club heads.

TABLE 1

Nine Point Pendulum Test Results SZ 440, Club W

| Club Model | PEN Center | PEN Toe | PEN Heel | PEN High Center | PEN High Toe | PEN High Heel | PEN Low Center | PEN Low Toe | PEN Low Heel |
|---|---|---|---|---|---|---|---|---|---|
| Comparative SZ 440 | 235 | 238 | 235 | 229 | 244 | 240 | 227 | 226 | 232 |
| Inventive Club W | 251 | 269 | 250 | 251 | 266 | 263 | 268 | 255 | 235 |

In accordance with another aspect of the present invention, the thickness of intermediate zone 6 or optional perimeter portion 8 on hitting face 2 can be thinly manufactured by removing the weld lines from the hitting face to the crown and sole of the club head. An alternate method for improving the performance of hitting face 2 is to remove weld lines and joints of face insert 42 to another surface of club head 10. As is known in the art, a weld line or joint is an area of discontinuity, where even if two pieces of the same material are joined, the structural properties of the pieces in the vicinity of the joint are altered. Removing weld lines to the crown or the sole of a club head allows the thickness of the hitting face to be controlled more precisely and allows for a thinner overall hitting face. The joints can also be used to alter the properties of the hitting face. In accordance with this aspect of the invention, the face insert may include one or more side walls, wherein the side walls may form part of the crown and/or part of the sole.

Figure 9:
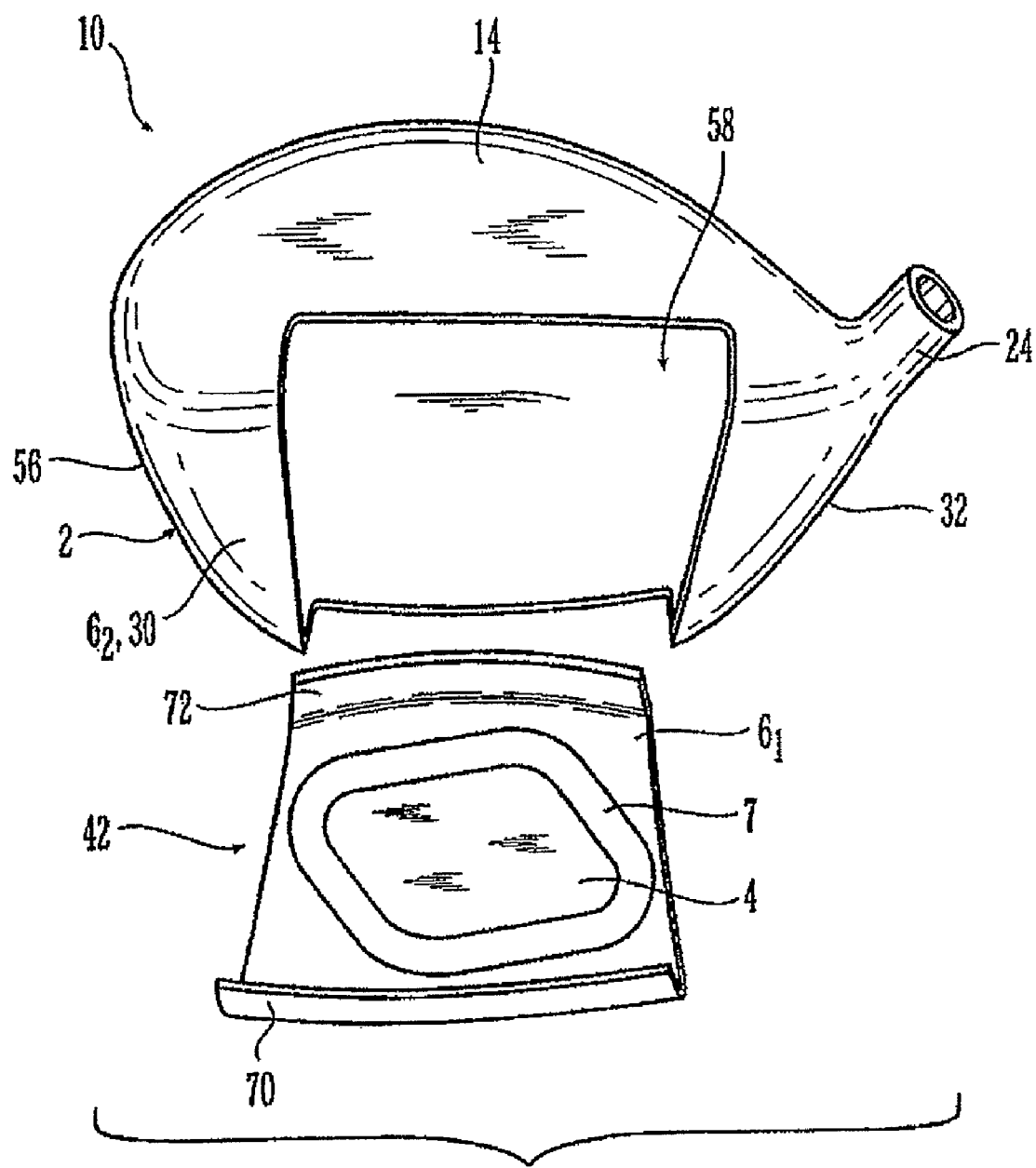
FIG. 9 is a front exploded view of an alternate embodiment of a club head.

Referring to FIG. 9, which corresponds to FIG. 9 from the parent case, face insert 42 comprises central zone 4, transition zone 7, a portion of intermediate zone 6, partial crown portion 54 and partial sole portion 56. Club head 10 correspondingly defines cavity 58 sized and dimensioned to receive face insert 42. Face insert 42 is preferably welded to club head 10. Face insert 42 together with face support 30 forms hitting face 2. Similar to the embodiment illustrated in FIG. 2, intermediate zone 6, designated as $6_1$ and $6_2$, can be disposed partially on face insert 42 and partially on face support 30.

Figure 10:
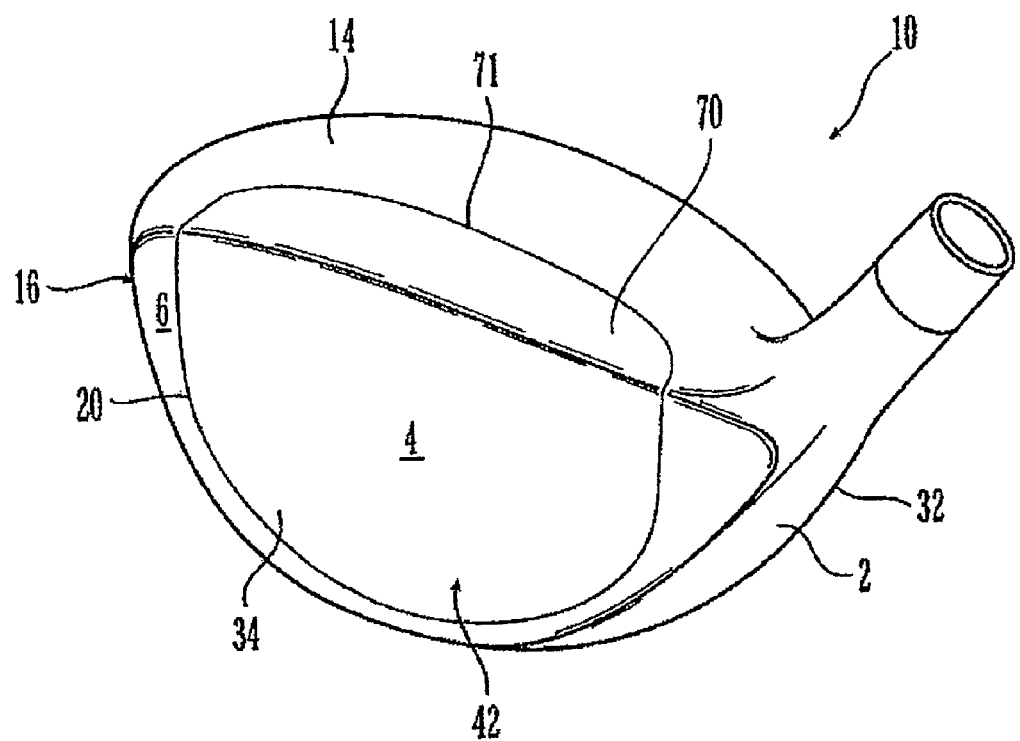
FIG. 10 is a perspective view of another alternate embodiment of a club head of the present invention.

Referring now to FIG. 10, another embodiment according to the present invention is shown. In this embodiment, central zone 4 of hitting face 2 is formed of a face insert 42. Face insert 42 is preferably welded to club head 10 along weld line 20. Face insert 42 includes a polygonal or elliptical main plate 34 and a sidewall or wing 70 that extends into and forms a part of crown 14. As such, an upper portion 71 of weld line 20 is removed to crown 14. As the stress line created by weld line 20 is removed from hitting face 2, the probability of failure along upper portion 21 due to repeated impact with golf balls is reduced.

Face insert 42 is preferably made from the same material as the rest of club head 10, such as titanium, a titanium alloy, steel, or any other material suitable for use as a club head. Face insert 42 is preferably the same thickness as the rest of club head 10, although face insert 42 may be made thicker or thinner in order to affect the flexural stiffness thereof.

Figure 11:
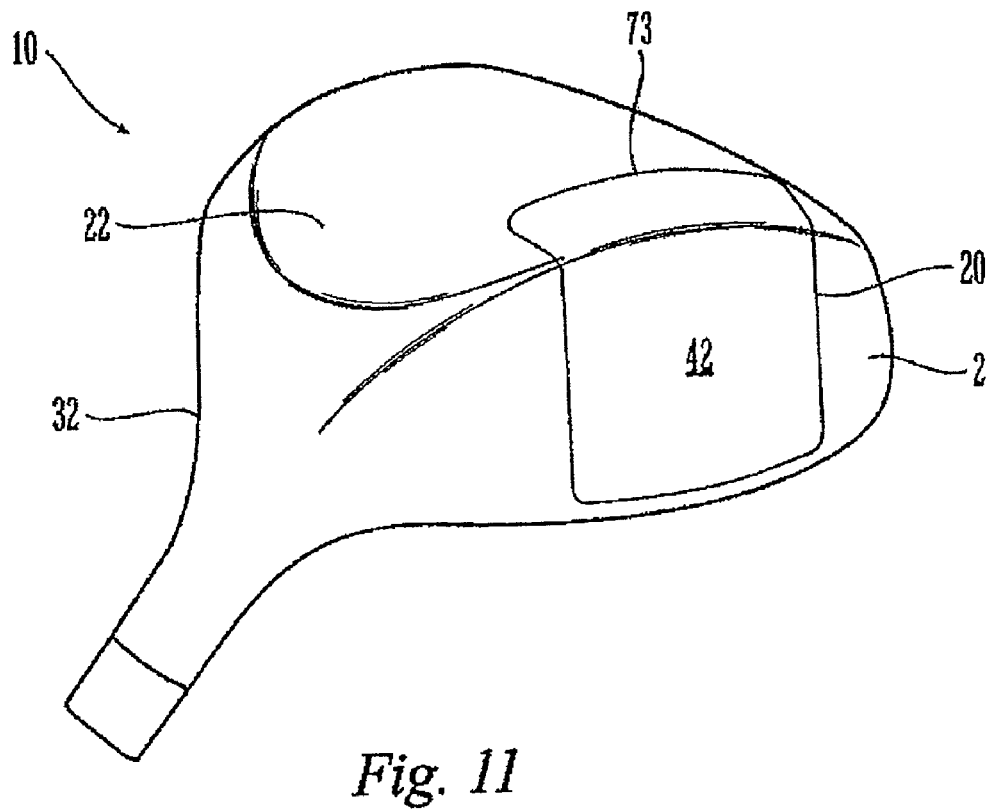
FIG. 11 is a perspective view of another alternate embodiment of a club head of the present invention.

The size and shape of face insert 42 may vary. As stated above, preferably, face insert 42 is a modified oval U-cup or L-cup, but it may also be other shapes, such as rectangular, elliptical or circular. Face insert 42 preferably forms nearly the entire surface area of hitting face 2. However, face insert 42 may form a much smaller portion of hitting face. Also, wing 70 may extend into and form a part of sole 22, as shown in FIG. 11, by simply inverting the configuration of face insert 42. In this case, the affected weld line is lower weld line 73.

The material properties of face insert 42 can also be affected by the method chosen to form face insert 42. For example, face insert 42 is preferably stamped from sheet metal after the metal has been cold rolled or cold worked in order to align the crystal grains of the metal. Stamping metal in this fashion produces a stronger hitting face than other manufacturing techniques. Further, face insert 42 is then positioned within hitting face 2 so that the grain flow pattern of face insert 42 runs in a sole-to-crown direction. Alternatively, the grain flow pattern of face insert 42 may run in a heel-to-toe direction or in a diagonal direction. Other methods known in the art may also be used to manufacture face insert 42, such as forging and casting.

Figure 12A:
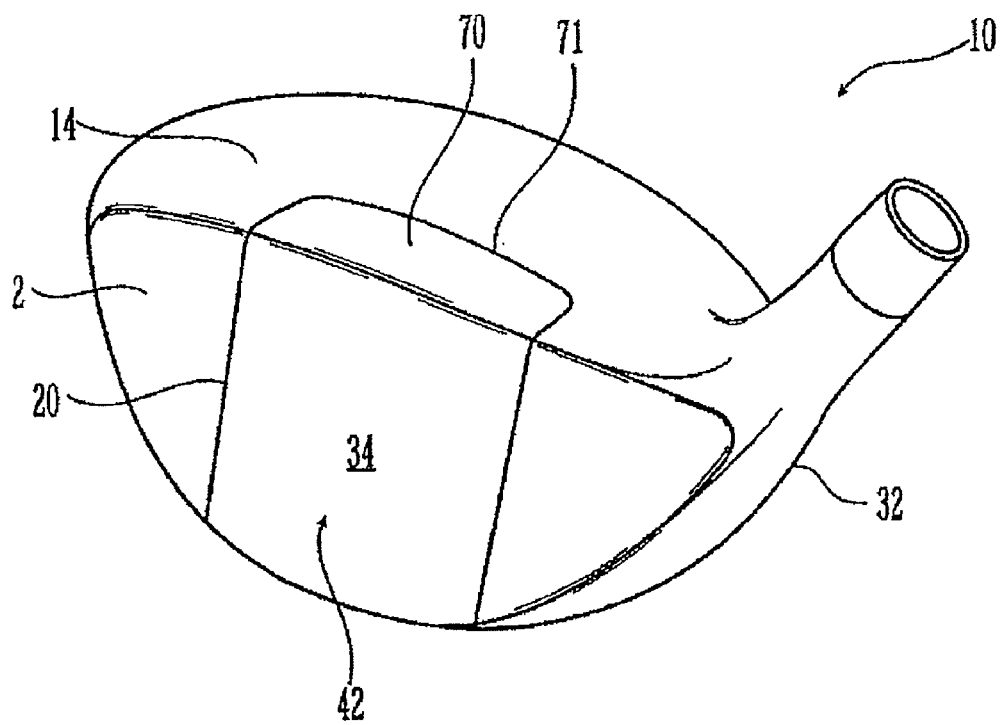
FIG. 12a is a top perspective view of another alternate embodiment of a club head of the present invention.
Figure 12B:
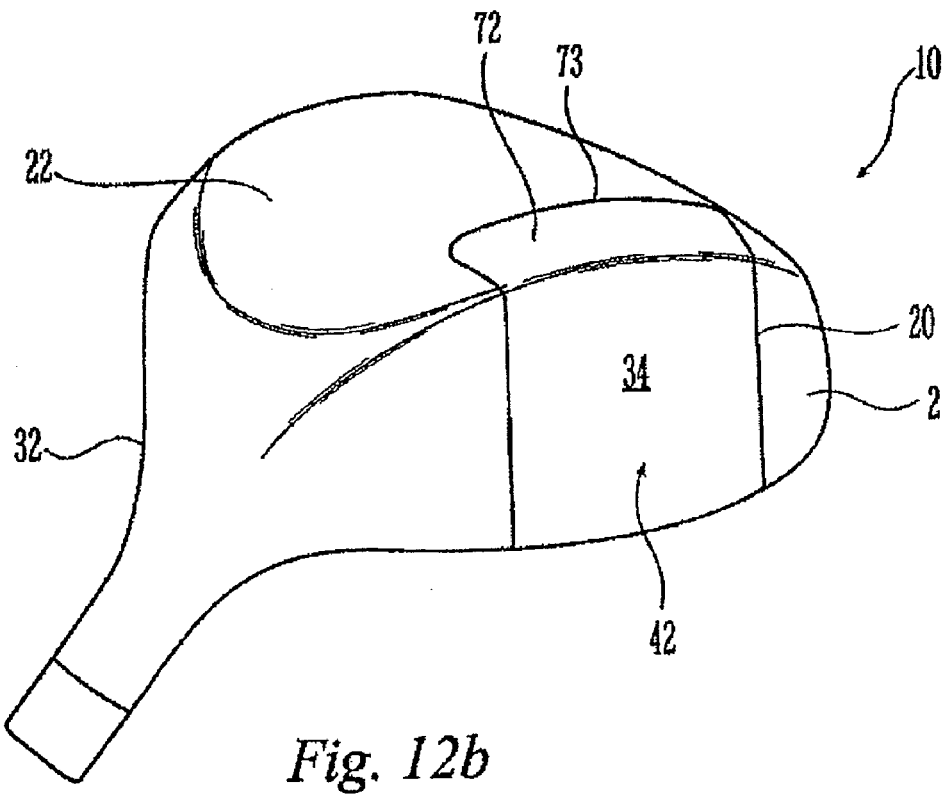

FIGS. 12a and 12b show another embodiment of club head 10 similar to the embodiment shown in FIG. 10. In this embodiment, face insert 42 includes a main plate 34, an upper sidewall or wing 70 that extends into and forms part of crown 14 as well as a lower wing 72 that extends into and forms part of sole 22. As such, upper weld line 71 and lower weld line 73 are removed to crown 14 and sole 22, respectively, so as to reduce the potential for failure thereof. All other aspects of face insert 42 are as described above with respect to FIG. 10.

Figure 13A:
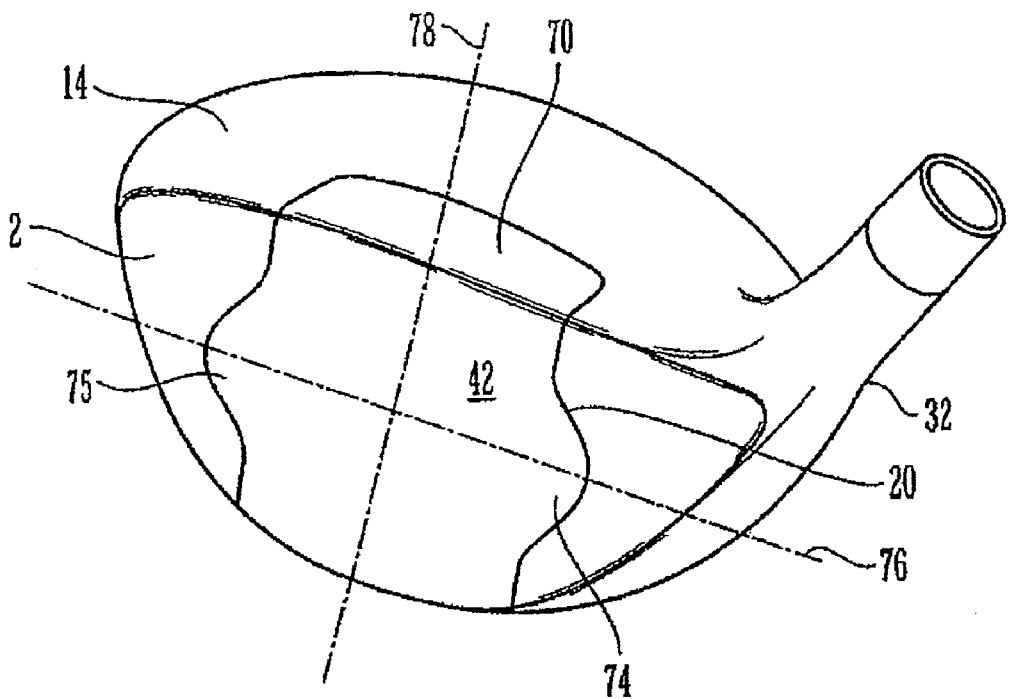
FIG. 13a is a top perspective view of another alternate embodiment of a club head of the present invention.
Figure 13B:
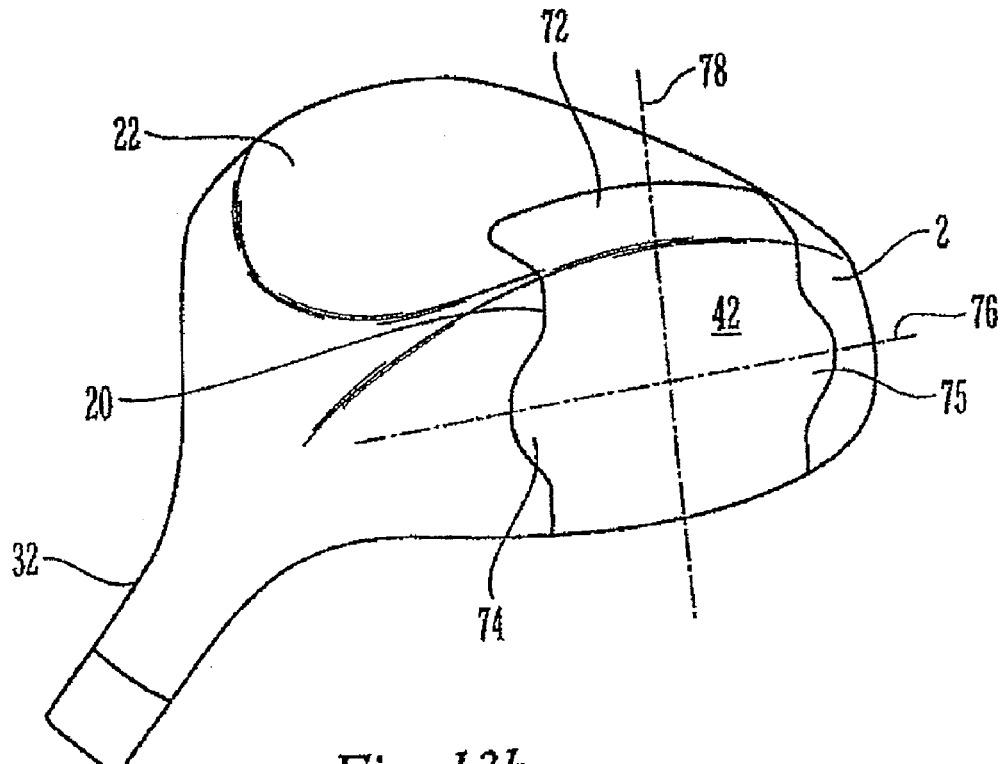

FIGS. 13a and 13b show yet another embodiment of club head 10 similar to the embodiment shown in FIG. 10. In this embodiment, face insert 42 includes an upper sidewall or wing 70 that extends into and forms part of crown 14, a lower sidewall or wing 72 that extends into and forms part of sole 22, a heel extension 74, and a toe extension 75. Upper wing 70 and lower wing 72 are as described above with respect to FIGS. 10, 12a, and 12b. Heel extension 74 and toe extension 75 are extensions of the main plate of face insert 42 along the horizontal axis 76 thereof at or near the center of the vertical axis 78 thereof. This alteration of the geometry of face insert increases the deflection capabilities of face insert 42 along horizontal axis 76 while vertical axis 78 has a different, lesser deflection capability.

Face insert 42 is preferably of a size and general shape as described above with respect to the embodiment shown in FIGS. 10, 12a and 12b, i.e., a polygonal or elliptical main plate that forms much of the surface area of hitting face 2. Upper wing 70 and lower wing 73 are preferably generally elliptical or polygonal, although other shapes are contemplated by the present invention. Similarly, heel extension 74 and toe extension 75 are preferably semi-elliptical in shape, although other shapes such as semi-circular are contemplated by the present invention. As such, the preferred geometry of face insert 42 is a central oval having a long axis along horizontal axis 76 of hitting face 2 and generally rectangular extensions stretching along vertical axis 78 of hitting face 2. Further, one of heel extension 74 and toe extension 75 may be eliminated. Also, one or both of upper wing 70 and lower wing 73 may be eliminated. Further, face insert 42 may incorporate a dense insert as shown in any of the embodiments shown in FIGS. 3-8 for increased performance effects. Face insert 42 may also contain central zone 4 and intermediate zone 6, where the flexural stiffness of central zone 4 is higher then the flexural stiffness of intermediate zone 6, as described above and as described in the parent application and in the grandparent '007 patent. Additionally, central zone 4 may also include a dense insert 52 as described above.

Hitting face 2 is preferably milled or stamped and milled. The body of club 10 is preferably cast. The inner cavity of club head 10 may be empty, or alternatively may be filled with foam or other low specific gravity material. It is preferred that the inner cavity has a volume greater than 250 cubic centimeters, and more preferably greater than 275 cubic centimeters, and most preferably 350 cubic centimeters or more. Preferably, the mass of the inventive club head is greater than 150 grams but less than 220 grams. Further part and manufacturing details and additional test results regarding the COR values of inventive club heads are discussed in detail in the parent case.

Yet another parameter that reflects the stiffness of a structure is inertance. Generally, inertance is a frequency response. More specifically, inertance reflects the stiffness of a structure, in this instance the club face, at various frequencies of vibration. The units of inertance are acceleration units over force units. A preferred first resonant frequency for the inventive club face described herein is located where inertance is maximized. The testing methodology and apparatus for determining inertance are described in further detail in the parent patent, U.S. Pat. No. 6,605,007, which patent is incorporated herein in its entirety by reference.

Figure 14:
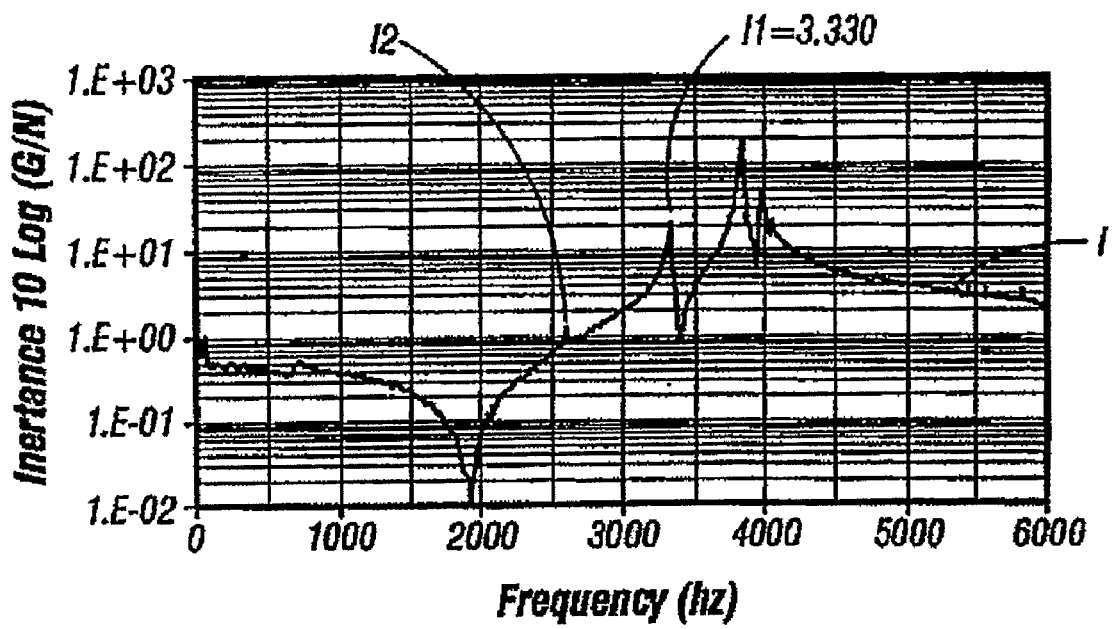
FIG. 14 is a graph of inertance versus frequency for a conventional club head.

Referring to FIG. 14, a graph of inertance versus frequency for a conventional club head is shown. The conventional club head is a Callaway Great Big Bertha War Bird with an eight degree loft. The point I1 at a frequency of 3330 Hertz represents the first primary resonant frequency which occurs at the first primary maxima inertance for the inertance function I. A maxima which does not represent a primary resonant natural frequency of the face is also present in FIG. 14 at a frequency of 2572 Hertz, which is designated as point I2. These secondary maxima I2 are characterized by inertance transitions of a magnitude of less than 10 decibels. These secondary maxima may be due to crown, sole or skirt vibrations that are not acting perpendicular to the plane of the club face. Secondary maxima do not correlate with COR and ball velocity, since the vibration response is either small in magnitude or alternately not coincident with ball response. The COR for the convention club head tested was measured in accordance with USGA, Rule 4-1e Appendix II Revision 2 dated Feb. 8, 1999 and was found to be 0.785. The preferred first primary resonant frequency of vibration is defined by the following relationship:

$$1/(2*\text{contact duration}) < I1 < 3/(2*\text{contact duration})$$

The contact duration is the time interval during which the ball is in contact with the club face. The contact duration for a typical driver impact is about 500 microseconds. Thus, the preferred primary resonant frequency of vibration for the conventional club head is between about 1000 and 3000 Hertz. The closer the COR is to the lower limit, the higher the COR and thus the higher the rebound ball velocity. More preferably, the first primary resonant frequency is less than 2900.

Figure 15:
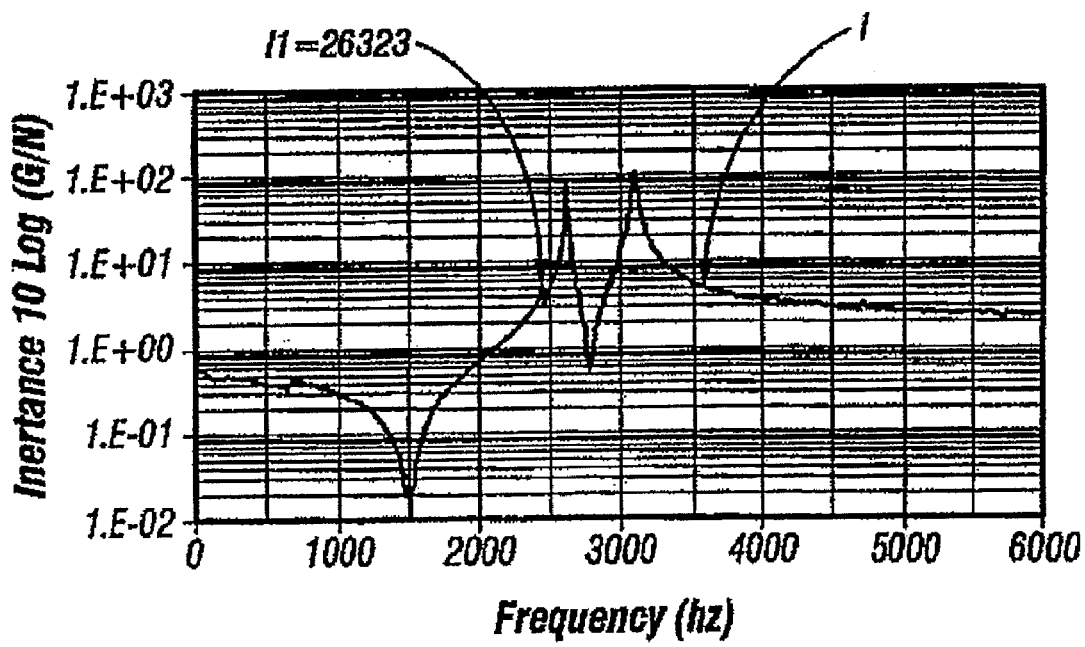
FIG. 15 is a graph of inertance versus frequency for the inventive club head discussed in priority case.

FIG. 15 illustrates the inertance function of the inventive club head described and claimed in priority U.S. Pat. No. 6,605,007 ("the '007 club"). The first primary resonant frequency of vibration for the club head is at 2632 Hertz, and the COR of the '007 club was measured to be 0.824. The COR of the '007 club was measured to be 0.824. The COR of the '007 club is greater than the conventional club of FIG. 14, and therefore will provide greater ball rebound velocity.

The overall flexural stiffness of a club head and the distribution of the flexural stiffness across the face of the club head impact the resonant frequency of a club head. Furthermore, the swing speed will determine if the club and/or a golf ball vibrates at the resonant frequency upon impact. As such, by altering the structural design and properties of a club head, a club designer may alter the resonant frequency of the club head to coordinate with the resonant frequency of a particular golf ball so as to maximize the distance traveled by the ball when struck at a certain swing speed. Also, if the club is designed with a particular golfer in mind, the club can be designed to resonate upon striking a particular golf ball at the golfer's average swing speed. For example, if the club and the ball resonate at a similar frequency, if they strike each other so as to produce resonance, then the vibrations of both club and ball act to push the ball off of the club face faster. Preferably, the resonance frequency of the club is 0-20% greater than the resonant frequency of the ball. More preferably, the resonance frequency of the club is 0-10% greater than the resonant frequency of the ball.

While various descriptions of the present invention are described above, it should be understood that the various features of each embodiment could be used alone or in any combination thereof. Therefore, this invention is not to be limited to only the specifically preferred embodiments depicted herein. Further, it should be understood that variations and modifications within the spirit and scope of the invention might occur to those skilled in the art to which the invention pertains. For example, the face and/or individual zones can have thickness variations in a step-wise or continuous fashion. Other modifications include a perimeter zone that has a thickness that is greater than or less than the adjacent, intermediate zone. In addition, the shapes of the central, intermediate, and perimeter zones are not limited to those disclosed herein. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

We claim:

1. A golf club head comprising:
   a hitting face comprising
   a central zone formed in part of a first material, wherein the central zone has a first flexural stiffness; and
   an intermediate zone concentric with the central zone, wherein the intermediate zone is formed from a second material that is different from the first material, wherein the intermediate zone has a second flexural stiffness, and wherein the first flexural stiffness is higher than the second flexural stiffness such that on ball impact, deformation of the intermediate zone allows the central zone to move into and out of the club as a unit and the club exhibits a primary natural frequency of less than 2900 Hertz wherein the second material forms a plate-like face having a geometric center and the first material forms an insert fixedly attached to the second material at or near the geometric center.

2. The golf club head of claim 1, wherein the central zone comprises about 15% to 60% of the hitting face and is formed in part of a first material disposed on an inner surface of the hitting face.

3. The golf club head of claim 1, wherein the plate-like face is configured to receive at least a portion of the first material at or near the geometric center.

4. The golf club head of claim 3, wherein the plate-like face includes a void formed there through at or near the geometric center configured to receive at least a portion of the first material.

5. The golf club head of claim 3, wherein the plate-like face includes a hollow protrusion formed at or near the geometric center configured to receive at least a portion of the first material.

6. The golf club head of claim 5, wherein the protrusion includes an overhang formed around a perimeter of the protrusion, wherein the overhang is configured to hold at least a portion of the second material within the protrusion.

7. The golf club head of claim 1, further comprising a hollow cap formed of the second material, wherein the first material forms a plug that is inserted into the hollow cap and the cap is fixedly attached to the plate-like face.

8. The golf club head of claim 7, wherein the hollow cap is welded to the plate-like face.

9. The golf club head of claim 7, wherein the hollow cap is affixed to the plate-like face using an adhesive.

10. The golf club head of claim 7, wherein the plug is affixed to an interior surface of the hollow cap.

* * * * *